United States Patent [19]

Platel et al.

[11] Patent Number: 4,500,531

[45] Date of Patent: Feb. 19, 1985

[54] THERAPEUTICAL USE OF (1-CINNAMOYL OR 1-PHENETHYLCARBONYL) PIPERAZINE DERIVATIVES

[75] Inventors: Alain Y. Platel, Rueil Malmaison; Alain P. Lacour, La Varenne; Guy R. Bourgery, Colombes, all of France

[73] Assignee: Delalande S.A., Courbevoie, France

[21] Appl. No.: 461,701

[22] Filed: Jul. 27, 1983

[30] Foreign Application Priority Data

Feb. 4, 1982 [IT] Italy ................ 19457 A/82

[51] Int. Cl.³ .......................................... A61K 31/495
[52] U.S. Cl. ................................................. 514/255
[58] Field of Search ........................................ 424/250

[56] References Cited

U.S. PATENT DOCUMENTS 3,634,411  1/1972  Fauran et al. .................. 542/440

Primary Examiner—Stanley J. Friedman
Attorney, Agent, or Firm—Flynn, Thiel, Boutell & Tanis

[57] ABSTRACT

A class of known (1-cinnamoyl or 1-phenylethylcarbonyl) piperazine derivatives have been found to be central nervous system stimulants effective to improve the mental alertness and to brighten the spirits of human beings.

6 Claims, No Drawings

THERAPEUTICAL USE OF (1-CINNAMOYL OR 1-PHENETHYLCARBONYL) PIPERAZINE DERIVATIVES

The present invention concerns the therapeutic use of known (1-cinnamoyl or 1-phenethylcarbonyl)piperazine derivatives and the pharmacologically acceptable acid addition salts thereof.

More precisely, the derivatives employed in the invention have the following formula:

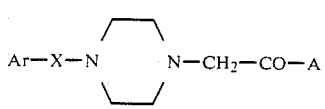

wherein Ar represents:
either the 3,4,5-trimethoxyphenyl group, in which case X represents:
the 2-propen 1-one ylene chain of trans configuration

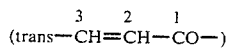

linked to Ar through its carbon atom 3, A being a group chosen from the following ones:

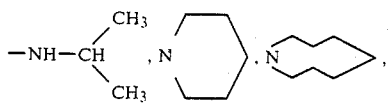

the 2-propen 1-one ylene chain of cis configuration

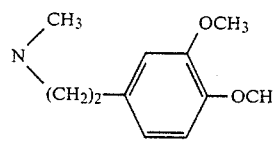

linked to Ar through its carbon atom 3, A being the

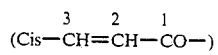

or
the propan 1-one ylene chain

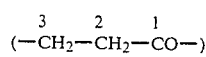

linked to Ar through its carbon atom 3, A being the

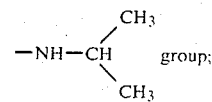

or the 3,5-dimethoxy-4-hydroxy phenyl group, in which case X represents the 2-propen 1-one ylene chain of trans configuration

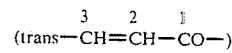

linked to Ar through its carbon atom 3 and A is the

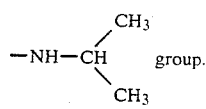 group.

The derivatives of formula (I) in which Ar represents the 3,4,5-trimethoxyphenyl group, X represents the 2-propen 1-one ylene chain of trans configuration and A represents a group chosen from the following ones:

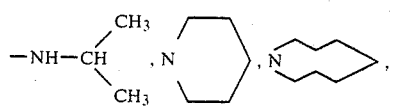

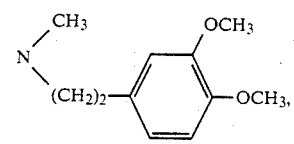

as well as the salts thereof, are described in U.S. Pat. Nos. 3,634,411 and 4,029,650 as having peripheral, coronary and/or vasodilatory activities.

The above-mentioned patents also describe a process for preparing these derivatives and salts and some physico-chemical data of the latter. According to this process, the starting product, namely the N-(3,4,5-trimethoxy cinnamoyl)N'-(carboxymethyl)piperazine is reacted with the appropriate amine. The melting points given in the examples appearing in the above-mentioned U.S. patents all correspond to compounds of trans configuration.

The derivative of formula (I) having the particular structure:

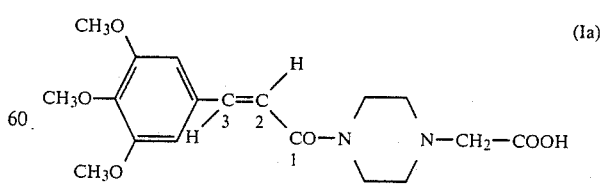

(trans configuration)

and the salts thereof are described in Arzneim. Forsch. 22, 1726 (1972) as being non-active metabolites of the compound of formula:

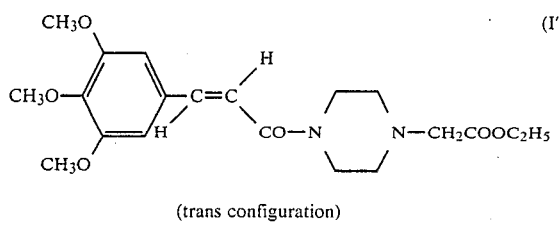

(trans configuration)

and of its salts, which are peripheral and coronary vasodilators.

The derivative of formula (Ia) and the salts thereof are obtained:
- either by saponifying, preferably by aqueous NaOH, the derivative of formula (I'a), which can be followed by salification,
- or by condensing chloracetic acid with N-(3,4,5-trimethoxy)cinnamoyl piperazine of trans configuration, which can be followed by salification.

The derivative of formula (I) having the particular structure:

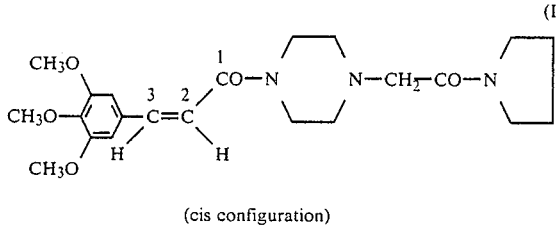

(cis configuration)

and the salts thereof are described in XENOBIOTICA 6, 441 (1976) as being non-active degradation products of the compound of formula:

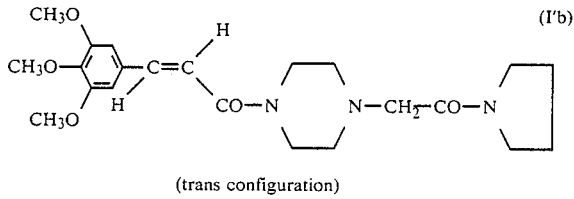

(trans configuration)

and the salts thereof, which are peripheral and coronary vasodilators.

The derivative of formula (Ib) and its salts can be obtained by photochemical isomerization of the compound of formula (I'b) and of the salts of the latter.

The derivative of formula (I) having the particular structure:

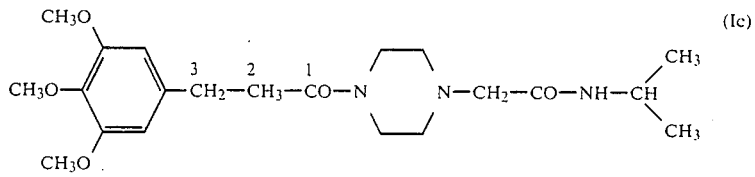

and the salts thereof are described in French Pat. No. 2 262 521 as being peripheral and coronary vasodilators, said French patent also describing the process of preparation and some physico-chemical data of this derivative and its salts.

Finally, the derivative of formula (I) having the particular structure:

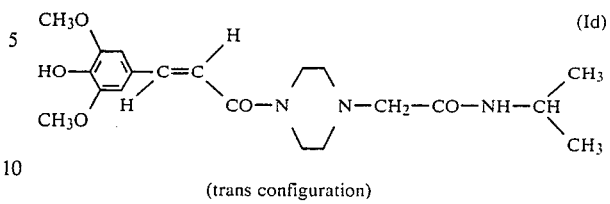

(trans configuration)

is described in French Patent No. 2 244 518 as being a coronary vasodilator. Said patent also describes a process for preparing this derivative and some physico-chemical data of the latter. According to this process, 4-acetoxy 3,5-dimethoxy 1-propenyloic benzene acid chloride is reacted with N-(isopropylamino carbonyl methyl)piperazine, the resulting compound being hydrolyzed by means of aqueous NaOH. The melting point given in the example of this French patent shows that the obtained compound is of trans configuration.

The examples given hereafter illustrate the preparation of a derivative of formula (Ia) and of a derivative of formula (Ib).

EXAMPLE 1 trans 1-(3,4,5-trimethoxy)cinnamoyl 4-hydroxycarbonylmethyl piperazine, hydrochloride (Ia)

A suspension of 10 g of trans 1-(3,4,5-trimethoxy)cinnamoyl 4-ethoxy-carbonylmethyl piperazine (I'a) in 25 ml of aqueous NaOH (1N) is brought to 65° C. in order to obtain a solution. Then the reaction medium is acidified (pH≃5.6) by means of HCl (1N), the reaction medium is then filtered and the obtained product is recrystallized in 90% acetone. 8.7 g (Yield≃87%) of the expected compound are obtained.

Melting point: 164° C.
Empirical formula: $C_{18}H_{25}ClN_2O_6$
Molecular weight: 400.85

EXAMPLE 2 trans 1-(3,4,5-trimethoxy)cinnamoyl 4-hydroxycarbonylmethyl piperazine, hydrochloride (Ia)

A suspension of trans N-(3,4,5-trimethoxy)cinnamoyl piperazine (37 g), triethylamine (12.5 g) and chloroacetic acid (11.5 g) in 300 ml of methylethylketone is held at reflux for 8 hours. Then the reaction medium is diluted with water (200 ml), the aqueous layer is decanted, the organic layer is acidified by means of concentrated HCl and then is filtered. The formed precipitate is filtered and recrystallized in a water (60 ml)-acetone (500 ml) mixture, then in alcohol. 10 g (Yield≃20%) of the expected compound are obtained.

The compound has the same melting point as the compound obtained in example 1.

EXAMPLE 3 cis 1-(3,4,5-trimethoxy)cinnamoyl 4-pyrrolidinocarbonylmethyl)piperazine, oxalate (Ib)

A solution of 100 g of trans 1-(3,4,5-trimethoxy)cinnamoyl 4-pyrrolidinocarbonylmethyl piperazine oxalate (I'b) in 2000 ml of water, distributed in 100 white glass ampoules of 2 ml, is isomerized during 108 hours in a light irradiation chamber (7,400,000 lux-hour). Then the solution is filtered, neutralized by means of potassium carbonate, extracted with ethyl acetate and dried on sodium sulfate. The obtained solution is then filtered and the filtrate is evaporated. The residue is dissolved in acetone, added with an acetone solution of oxalic acid, the precipitate is filtered and recrystallized in acetone. The expected compound is thus obtained with a yield of 75%.

Melting point: 118° C.
Empirical formula: $C_{24}H_{33}N_3O_9$
Molecular weight: 507.53
Elementary analysis:

|  | C | H | N |
|---|---|---|---|
| Calculated (%) | 56.79 | 6.55 | 8.28 |
| Found (%) | 56.49 | 6.40 | 8.05 |

Table I below shows the compounds employed in the present invention.

TABLE 1

$$Ar-X-N\underset{}{\overset{}{\bigcirc}}N-CH_2-CO-A \quad (I)$$

| Code Number | Ar— | —X— | —A | Form | Empirical formula | Molecular weight | Melting Point (°C.) | | ELEMENTARY ANALYSIS % | | |
|---|---|---|---|---|---|---|---|---|---|---|---|
| | | | | | | | | | C | H | N |
| 65 | 3,4,5-tri(CH$_3$O)-phenyl with CH$_3$ | —CH=CHCO— (trans) | —NH—CH(CH$_3$)$_2$ | Base | C$_{21}$H$_{31}$N$_3$O$_5$ | 405.48 | 175 | Cal. Obt. | 62.20 62.40 | 7.71 7.66 | 10.36 10.31 |
| 66 | " | —CH=CHCO— (trans) | piperidine | " | C$_{23}$H$_{33}$N$_3$O$_5$ | 431.52 | 172 | Cal. Obt. | 64.01 64.27 | 7.71 7.85 | 9.74 9.76 |
| 67 | " | —CH=CHCO— (trans) | octahydroazocine | " | C$_{25}$H$_{37}$N$_3$O$_5$ | 459.57 | 116 | Cal. Obt. | 65.33 65.47 | 8.12 8.28 | 9.14 9.39 |
| 68 | " | —CH=CHCO— (trans) | 3,4-dimethoxyphenethyl-N(CH$_3$)— | " | C$_{29}$H$_{39}$N$_3$O$_7$ | 541.63 | 138 | Cal. Obt. | 64.30 64.36 | 7.26 7.13 | 7.76 7.76 |
| 69 | 3,5-di(CH$_3$O)-4-OH-phenyl | —CH=CHCO— (trans) | —NH—CH(CH$_3$)$_2$ | " | C$_{20}$H$_{29}$N$_3$O$_5$ | 391.45 | 204 | Cal. Obt. | 61.36 61.38 | 7.47 7.32 | 10.74 10.66 |
| 70 | 3,4,5-tri(CH$_3$O)-phenyl | —CH$_2$—CH$_2$—CO— | " | Maleate | C$_{25}$H$_{37}$N$_3$O$_9$ | 523.57 | 114 | Cal. Obt. | 57.35 57.20 | 7.12 7.09 | 8.03 7.93 |
| 71 | " | —CH=CH—CO— (trans) | —OH | HCl | C$_{18}$H$_{25}$ClN$_2$O$_6$ | 400.85 | 164 | Cal. Obt. | — — | — — | — — |
| 72 | " | —CH=CHCO— (cis) | pyrrolidine | Oxalate | C$_{24}$H$_{33}$N$_3$O$_9$ | 507.53 | 118 | Cal. Obt. | 56.79 56.49 | 6.55 6.40 | 8.28 8.05 |

A thorough pharmacological study of the derivatives of formula (I) and the salts thereof, has now revealed that the derivative of formula (Ia) and the derivative of formula (Ib), which have been considered, up to the present, to be inactive in the pharmacological field, possess important activities in the stimulation or protection of cerebral functions. This study has also shown that the other derivatives of formula (I), i.e., those known for their vasodilatory activities, also possess the same activities in the stimulation or protection of cerebral functions.

The stimulating or protecting activities have been shown particularly by the test of the mnesic retention of exploratory activity carried out in accordance with the following method: in an ACTIMETRE APELAB apparatus (BOISSIER and SIMON, Arch. Inter. Pharmacodyn. 158, 212, (1965), the exploratory activity of SWISS-WEBSTER male mice was measured for 5 minutes, then the animals were given an intraperitoneal injection or oral administration of the derivatives of formula (I), the salts thereof or of physiological serum. After a week, the exploratory activity of the treated animals is again measured and the effect of the mnesic retention is measured by an habituation, i.e., by a statistically significant reduction (t of STUDENT in paired groups) of the exploratory activity.

To illustrate the invention, in Table II below the results thus obtained are given.

It should be noted that the activities for stimulating or protecting the cerebral functions may also be shown by the oxygen pressure test ($PO_2$) of the sub-cortical tissues, effected on awake rabbits maintained under normoxemia according to the following method.

The calvarium is disengaged after anaesthesia with NEMBUTAL, then a unilateral opening is made in the skull, a platinum electrode is introduced into the cortex at a point anterior to the coronary suture (5 mm) and a reference chlorinated silver electrode is placed subcutaneously. After the animals were allowed to rest for one month after implantation of the electrodes, the derivatives of formula (I) and the salts thereof are administered to them intravenously and the variation of the sub-cortical tissue $PO_2$ caused by this administration and the duration of the action are measured. The sub-cortical tissue $PO_2$ is evaluated by the polarographic method (TRANSIDYNE apparatus) and is recorded on a potentionmetric recorder.

Similarly, the new activities in accordance with the invention can be shown by the test of the antagonism of the hypomotilizing effect of normobar hypoxemia (8% oxygen) carried out on mice, in accordance with the following method.

The number of displacements are measured of a mouse placed for 5 minutes in a circular closed enclosure in which the oxygen content of the ambient air is maintained at 8%. Under these conditions, we observe for untreated control mice a considerable reduction in the number of displacements. On the contrary, the derivatives of formula (I), and the salts thereof administered intraperitoneally 30 minutes before the measurement, increase in a significant way (p√0.05, DUNNET's test) the average number of displacements of a batch of mice with respect to that of a batch of mice that received water intraperitoneally.

The approximate acute toxicity is determined according to the method described by MILLER and TAINTER in Proc. Soc. Exp. Biol. Med. 57, 261, (1944). The results obtained are also shown in Table II.

TABLE II

| Code Number of the tested compound | Dose (mg/kg/ i.p.) | % of the diminution of the exploratory activity | Acute toxicity $LD_{50}$ (mg/kg/i.v., i.p. or p.o.) |
| --- | --- | --- | --- |
| 65 | 10 | 17.9 | 475 (i.v.) |
| 66 | 3 | 35.2 | 2250 (p.o.) |
| 67 | 3 | 26.4 | 225 (i.v.) |
| 68 | 10 | 15.8 | 200 (i.v.) |
| 69 | 3 | 23.8 | 2000 (p.o.) (lethality = 0%) |
| 70 | 30 | 16.2 | 2000 (p.o.) (lethality = 0%) |
| 71 | 1 | 31.9 | 1000 (p.o.) (lethality = 0%) |
| 72 | 3 | 21.0 | — |

As the results of Table II show more especially, the differences between the toxic doses and the effective doses are sufficient to allow the derivatives of formula (I), and the salts thereof to be used in therapeutics, in particular for stimulating the intellectual efficiency in a normal subject, for preserving the cerebral functions in aged subjects and for treating vigilance and memorization troubles subsequent to different pathologies, particularly brain trauma, cerebral disturbances or acute or subacute cerebro-vascular accidents.

The derivatives of formula (I) and their salts will be administered preferably in the form of therapeutical compositions containing at least one of these derivatives or salts in association with a pharmacological acceptable vehicle. Thus, these derivatives or salts, can for example, be administered:

orally in the form of a solid like tablets, capsules, pellets for example, which comprises vehicles (such as cellulosic derivatives, vinylic polymers or gums for example) allowing modulation of drug release; depending upon the vehicle, this solid form gives a prompt or a slow release of the drug, orally in the form of aqueous solutions or suspensions (vehicles=water) or in the form of partially aqueous solutions or suspensions (vehicles=water+alcohols, glycerine or polypropylene glycol, for example), or parenterally in the form of injectable solutions freeze drying products or injectable suspensions.

The compounds employed in the invention can be administered orally in a total daily quantity up to 2.5 g/day taken in one or several doses (up to 6 doses) and parenterally in a total daily dose up to 1 g (1 to 3 injections per day).

The embodiments of the invention in which an exclusive property or privilege is claimed are defined as follows:

1. The method of stimulating or protecting cerebral function in a human being in order to increase mental alertness and capacity and to improve the focus on and performance of mental tasks, which comprises administering internally to a human being requiring such treatment a therapeutically effective amount of a compound of the formula

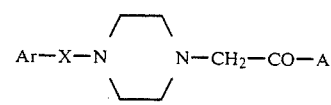

wherein Ar is selected from the group consisting of 3,4,5-trimethoxyphenyl and 3,5-dimethoxy-4-hydroxyphenyl, and, when Ar is 3,4,5-trimethoxyphenyl, the pair X and A are selected from the group consisting of (a) X is trans-CH=CH—CO— linked to Ar through its carbon atom 3, and A is

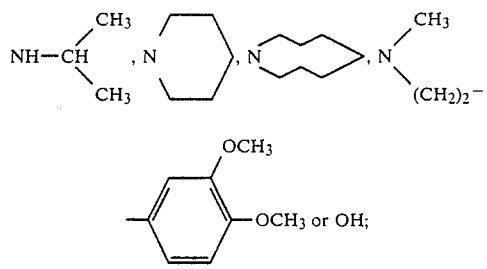

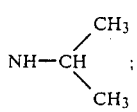

(b) X is cis-CH=CH—CO— linked to Ar through its carbon atom 3 and A is

and (c) X is —CH₂—CH₂—CO— linked to Ar through its carbon atom 3, and A is

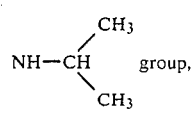

and when Ar is 3,5-dimethoxy 4-hydroxy phenyl group, X is trans—CH=CH—CO— linked to Ar through its carbon atom 3 and A is the NH—CH(CH₃)₂ group, or a pharmacological acceptable acid addition salt of said compound.

2. The method of claim 1, in which the compound is mixed with a pharmaceutically acceptable carrier.

3. The method of claim 1, in which the compound is administered orally or parenterally.

4. A method according to claim 1, in which the drug is administered orally, the therapeutically effective amount being up to 2.5 g/day taken in 1 to 6 divided doses.

5. A method according to claim 1, in which the drug is administered parenterally, the therapeutically effective amount being up to 1 g/day administered in 1 to 3 injections per day.

6. A method according to claim 1 in which said compound is selected from the group consisting of

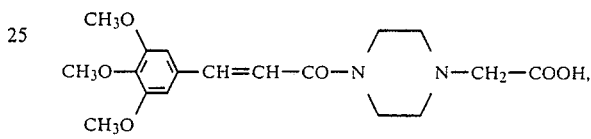

(trans)

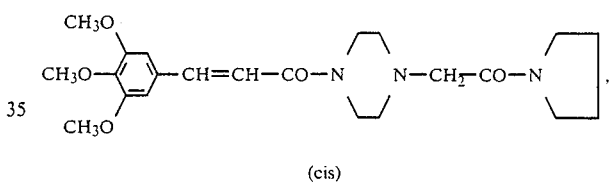

(cis)

and pharmaceutically acceptable acid addition salts thereof.

* * * * *